United States Patent
Bahia et al.

[11] Patent Number: 6,075,177
[45] Date of Patent: Jun. 13, 2000

[54] WOUND DRESSING

[75] Inventors: Hardev Singh Bahia; Thomas Richard Burrow, both of Coventry, United Kingdom

[73] Assignee: Acordis Fibres (Holdings) Limited, Derby, United Kingdom

[21] Appl. No.: 08/862,478

[22] Filed: May 23, 1997

Related U.S. Application Data

[63] Continuation of application No. 08/464,850, filed as application No. PCT/GB94/00114, Jan. 20, 1994, abandoned.

[51] Int. Cl.[7] .................................................... A61F 13/00
[52] U.S. Cl. ............................. 602/43; 602/56; 602/41; 536/56; 106/163.1
[58] Field of Search .............................. 602/43, 41, 56; 536/56; 106/163.1

[56] References Cited

U.S. PATENT DOCUMENTS

| | | |
|---|---|---|
| 244,644 | 7/1881 | Bahia et al. . |
| 1,736,714 | 11/1929 | Lilienfield . |
| 3,005,456 | 10/1961 | Graham . |
| 3,723,413 | 3/1973 | Chatterjee et al. . |
| 3,731,686 | 5/1973 | Chatterjee . |
| 3,847,636 | 11/1974 | Smith . |
| 3,858,585 | 1/1975 | Chatterjee . |
| 4,044,766 | 8/1977 | Kaczmarzyk et al. . |
| 4,200,557 | 4/1980 | Chatterjee et al. . |
| 4,246,221 | 1/1981 | McCorsley . |
| 4,410,694 | 10/1983 | Nakayama et al. . |
| 4,421,583 | 12/1983 | Aldred et al. . |
| 4,524,064 | 6/1985 | Nambu ........................ 424/81 |
| 4,538,603 | 9/1985 | Pawelchak et al. . |
| 4,579,943 | 4/1986 | Kamide et al. . |
| 4,634,438 | 1/1987 | Sustmann et al. . |
| 4,634,439 | 1/1987 | Sustmann et al. . |
| 4,651,725 | 3/1987 | Kifune et al. . |
| 4,728,642 | 3/1988 | Pawelchak et al. . |
| 5,197,945 | 3/1993 | Cole et al. . |

FOREIGN PATENT DOCUMENTS

| | | |
|---|---|---|
| 227955 | 7/1987 | European Pat. Off. . |
| 236104 | 9/1987 | European Pat. Off. . |
| 243069 | 10/1987 | European Pat. Off. . |
| 509703 | 10/1992 | European Pat. Off. . |
| 3209126 | 10/1982 | Germany . |
| 49-055993 | 5/1974 | Japan . |
| 52-005393 | 6/1975 | Japan . |
| 56-015458 | 2/1981 | Japan . |
| 60-002707 | 6/1983 | Japan . |
| 3000825 | 1/1991 | Japan . |
| 3269144 | 11/1991 | Japan . |
| 1329693 | 9/1973 | United Kingdom . |
| 1394742 | 5/1975 | United Kingdom . |
| 1548678 | 7/1979 | United Kingdom . |
| 2027714 | 2/1980 | United Kingdom . |
| 2094802 | 9/1982 | United Kingdom . |
| 2103993 | 3/1983 | United Kingdom . |
| 2220881 | 1/1990 | United Kingdom . |
| 2259464 | 3/1993 | United Kingdom . |
| WO89/12471 | 12/1989 | WIPO . |
| WO93/12275 | 6/1993 | WIPO . |

OTHER PUBLICATIONS

S. Thomas, "Hydrocolloid Dressings", in Wound Management and Dressings, Chapter 8, pp. 55–61 [Thomas I].

T.Turner, "Hydrogels and Hydrocolloids—An Overview of the Products and Their Properties", in Advances in Wound Management, pp. 89–95.

S. Thomas, "Hydrocolloids—A Guide to the Composition, Properties and Uses of Hydrocolloid Dressings and the Commercial Presentations Available", J. of Wound Care, 1(2):27–30 (Jul./Aug., 1992) [Thomas II].

D. Perrier et al., "Catalysis of the Cellulose–Cyclic Urea Reactions by Built–in Acid Groups", Textile Research Journal, pp. 680–685 (Aug., 1971) [Perrier I].

D. Perrier et al., "Properties of Carboxymethylated Cotton Prepared in Nonaqueous Media", J. Applied Polyer Science, 17:3375–3389 (1973) [Perrier II].

*Primary Examiner*—Jerome W. Donnelly
*Assistant Examiner*—Kelvin E. Hart
*Attorney, Agent, or Firm*—Howson and Howson

[57] ABSTRACT

A wound dressing has its wound-contacting surface composed of a tow or strand of textile filaments at least 15 mm long or a fabric of textile filaments at least 3 mm long, substantially all of the filaments being non-crosslinked carboxymethylcellulose filaments capable of absorbing at least 15 times their own weight of 0.9% aqueous saline solution. The wound-contacting surface forms a swollen, transparent gel which retains sufficient fibrous character to be removable as a coherent dressing from the wound.

33 Claims, No Drawings

WOUND DRESSING

CROSS REFERENCE TO RELATED APPLICATION

This application is a continuation of Ser. No. 464,850, filed Jun. 29, 1995 which is PCT/GB94/00114 with filing date of Jan. 20, 1994 and claiming priority to British 9301258.01, of Jan. 22, 1993 now abandoned.

TECHNICAL FIELD

This invention relates to wound dressings, which term also includes bandages and swabs for application to wounds including wounds consequent upon surgical operations, and to the use of absorbent fibre in dressings. The invention is especially applicable to dressings for deep-seated or chronic wounds such as ulcers.

BACKGROUND ART

The use of absorbent materials, particularly absorbent polysaccharide materials, at the wound-contacting surface of wound dressings is known. Dressings comprising alginate fibres are described, for example, in GB-A-1394742, GB-A-2103993, U.S. Pat. No. 4,421,583, EP-A-227955, EP-A-236104, EP-A-243069 and WO-89/12471. GB-A-1329693 describes a dressing comprising a substrate bearing a haemostatic material comprising an alginate and a water-soluble polymer such as sodium carboxymethyl cellulose.

U.S. Pat. No. 3,731,686 describes an absorbent dressing including a compressed body comprised of absorbent fibres of an alkali metal salt of carboxyalkyl cellulose having an average degree of substitution greater than 0.35 carboxyalkyl radicals per anhydroglucose residue, said absorbent fibres of an alkali metal salt of carboxyalkyl cellulose being heat-treated so as to become insoluble but swellable in water at room temperature. The dressing is typically a tampon, sanitary napkin or diaper having a core of the compressed absorbent fibres. U.S. Pat. No. 3,589,364 relates to bibulous water-insoluble cellulosic fibres which retain the fibrous form of the original cellulose raw material and are prepared by wet-crosslinking fibres of a water-soluble carboxymethyl cellulose salt. The fibres are suggested for use in a tampon, surgical dressing, surgical sponge, catamenial napkin or diaper. U.S. Pat. No. 4,634,438 and U.S. Pat. No. 4,634,439 describe a hygienic pH-regulating product for topical application, particularly a catamenial device, comprising a homogeneous mass of carboxyalkyl-modified cellulose fibres of degree of substitution 0.01 to 0.30 wherein the carboxyalkyl groups are in the free acid form.

Wound dressings containing a water-absorbent polymer such as sodium carboxymethyl cellulose are described in GB-A-1548678 and EP-A-92999 and in the books "Wound Management and Dressings" by S. Thomas (The Pharmaceutical Press) at pages 55–61 and "Advances in Wound Management" edited by T. D. Turner et. al (J. Wiley) at pages 89–95, and in the article by S. Thomas in J. Wound Care, Vol. 1 (1992) No. 2, pages 27–30. These dressings, generally known as hydrocolloid dressings, contain the water-absorbent polymer in powder form in an elastomeric and/or adhesive matrix such as polyisobutylene; the resulting material forms the wound-contacting layer of the hydrocolloid dressing. The hydrocolloid dressing takes up wound fluid to form a gel that produces a moist environment which facilitates healing. The absorbent component of the dressing is also produced in the form of granules or paste for the treatment of small cavities.

DISCLOSURE OF INVENTION

According to the present invention, a wound dressing is characterised in that the wound-contacting surface thereof comprises carboxymethyl cellulose filaments capable of absorbing at least 15 times their own weight of 0.9% by weight aqueous saline solution (as measured by the free-swell absorbency test) to form a swollen transparent gel and that the dressing when thus swollen to form a transparent gel retains sufficient fibrous character to be removed as a coherent dressing from a wound. The filaments may be in the form of continuous filaments or cut fibre, for example staple fibre, or of strands or fabrics made therefrom. The strands can be any linear textile material formed from the filaments or fibre, for example a yarn, sliver, roving or rope. The carboxymethyl cellulose filaments can for example be used as a tow or as a fabric.

In the free-swell absorbency test, 0.5 g of the carboxymethyl cellulose filaments, which have been conditioned at 65% relative humidity and 20° C. before being tested, is dispersed in 30 cc 0.9% by weight aqueous saline solution and left for 5 minutes. The dispersion is then filtered through a sintered Mark 1 funnel of pore size 100–160 microns and is left for 5 minutes, or until it stops dripping, whichever is the longer. The water filtered through the funnel is weighed and the weight of water absorbed by the filaments is calculated by subtraction.

The tow, strand or fabric of carboxymethyl cellulose filaments forming the wound-contacting surface of the dressing is preferably capable of absorbing at least 25 times its own weight of 0.9% by weight aqueous saline solution as measured by the free-swell absorbency test. The carboxymethyl cellulose filaments are preferably at least 15 mm long, most preferably at least 30 mm long, although cut fibre of shorter staple length down to 6 mm or even 3 mm can be used in certain nonwoven fabric constructions.

Dressings according to the invention using carboxymethyl cellulose filaments at the wound-contacting surface have many of the advantages in wound-healing properties of known hydrocolloid dressings based on carboxymethyl cellulose powder and have additional advantages of being easier to handle and apply to a wound. The filaments do not need to be mixed with any other material such as the adhesive used in known hydrocolloid dressings. The dressings of the invention are also easier to remove from a wound without causing mess, or damage to the wound. A dressing in which the carboxymethyl cellulose filaments are used as the only layer covering the wound has the additional advantage that the dressing can form a transparent gel in use, allowing observation of the wound without disturbing the dressing.

The dressings of the invention are distinguished from materials described in U.S. Pat. No. 3,731,686 and U.S. Pat. No. 3,589,364 in that the carboxymethyl cellulose filaments used in the present invention need not be crosslinked in order to be effective. The fibres described in U.S. Pat. No. 3,731,686 and U.S. Pat. No. 3,589,364 are generally derived from natural cellulose sources, and they are most commonly short fibres such as wood pulp fibres. When carboxymethylated, such short fibres require crosslinking to prevent complete dissolution and to maintain a coherent structure. The crosslinked fibres are water-swellable but are not water-soluble. The non-crosslinked carboxymethyl cellulose filaments used in the present invention will partially dissolve in aqueous liquids just as the carboxymethyl cellulose powder in known hydrocolloid dressings does. When long filaments (at least 15 mm) are used according to the present invention they prevent complete dissolution of the dressing and give a gel which is sufficiently coherent to be removable in one piece. A dressing according to the invention containing somewhat shorter filaments which are not crosslinked but are held securely in a nonwoven fabric construction can also form a gel which is removable as a coherent dressing. Crosslinking may, however, be used to alter the properties of the filaments used in the present invention, for example to reduce or eliminate dissolution of the fibres.

The carboxymethyl cellulose filaments are generally prepared by reacting cellulose filaments with a strong alkali and with monochloroacetic acid or a salt thereof.

The preferred cellulose filaments are solvent-spun cellulose filaments spun from a solution of cellulose in a solvent, as opposed to regenerated cellulose fibres which are spun from a solution of a cellulose derivative (cellulose xanthate) which is re-converted to cellulose in a spin bath into which the fibres are spun. Examples of solvents for cellulose are tertiary amine N-oxides, N,N-dimethyl formamide/nitrogen tetroxide mixtures, dimethyl sulphoxide/paraformaldehyde mixtures and solutions of lithium chloride in N,N-dimethyl acetamide or N-methyl pyrrolidone. The preferred solvents for use in producing solvent-spun cellulose filaments are tertiary amine N-oxides. The production of solvent-spun cellulose filaments is described for example in U.S. Pat. No. 4,246,221 and U.S. Pat. No. 4,196,281 which give examples of preferred tertiary amine N-oxides. The solution of cellulose is spun through an air gap into a bath of a non-solvent for cellulose, usually water, where the cellulose is precipitated in fibre form.

The carboxymethyl cellulose filaments can alternatively be produced from regenerated cellulose filaments, cuprammonium rayon or cotton fibres but carboxymethyl cellulose filaments produced from solvent-spun cellulose have higher absorbency and superior physical properties. The absorbency of 0.9% by weight saline solution, as measured by the free-swell method, of carboxymethyl cellulose filaments derived from solvent-spun cellulose can for example be 20–40 grams per gram, combined with a tenacity in the range 25–15 cN/tex. Viscose rayon or cotton fibres carboxymethylated by the same process have absorbencies only in the range 8–13 g/g and a lower tenacity. Carboxymethyl cellulose filaments formed from polynosic viscose rayon have increased absorbency and tenacity compared to carboxymethyl cellulose filaments formed from other types of viscose rayon, but they have less absorbency and tenacity compared to carboxymethyl cellulose filaments formed from solvent-spun cellulose. Solvent-spun cellulose filaments have a substantially uniform structure across their cross-section and have greater crystallinity than regenerated cellulose or cotton fibres, which both have a structure which includes a relatively dense skin at the surface of the fibre.

When carrying out carboxymethylation the alkali and the monochloracetic reagent can be applied to the cellulose filaments simultaneously or sequentially. The cellulose filaments are preferably in the form of a tow, but they can alternatively be in the form of yarn, staple fibre or fabric, for example a woven, knitted or nonwoven fabric.

Any finish present on the tow, yarn, fibres or fabric should preferably be removed by scouring before the carboxymethylation reaction, particularly if it is a hydrophobic finish. The yarn, tow or fibre can be a blend of the cellulose filaments with another fibre such as polyester or nylon, which is unaffected by the carboxymethylation process. A tow can be of dry filaments as commercially sold or it can be a tow of never-dried filaments, that is filaments which have not been dried after filament formation. The rate of uptake of reagents by the filaments may be somewhat faster using never-dried filaments.

The alkali and the monochloroacetic reagent are preferably applied from aqueous solution or from solution in a mixture of water and a polar organic solvent. The alkali is preferably an alkali metal hydroxide such as sodium hydroxide or potassium hydroxide and is preferably used at a concentration of at least 2% by weight, most preferably 5% or more, up to 15% by weight, most preferably up to 10%. The monochloroacetic reagent is preferably used in salt form, usually the salt corresponding to the alkali used, for example sodium monochloroacetate with sodium hydroxide. The monochloroacetate is preferably used at a concentration of at least 5% by weight, most preferably at least 10%, up to 35% by weight, most preferably up to 25%.

The alkali, for example sodium hydroxide, and monochloroacetic reagent, for example sodium monochloroacetate, are preferably applied to the cellulose filaments simultaneously. A solution containing the required concentration of sodium hydroxide and sodium monochloroacetate can be prepared by mixing solutions of these reagents which have been separately prepared or by dissolving sodium hydroxide in a solution of sodium monochloroacetate. When preparing a reagent solution in aqueous organic solvent, sodium hydroxide can for example be dissolved in water at up to 35% by weight and sodium monochloroacetate at up to 45% by weight and the solutions can be diluted with an alcohol such as ethanol or industrial methylated spirits to give the required concentration of reagents in the aqueous organic solvent mixture. The mixed solution can be applied by immersion of the filaments in the reagent solution in a reaction vessel at elevated temperature, for example at least 50° C. up to the boiling point of the solution, for a time sufficient to carry out the carboxymethylation reaction, for example from 10 minutes to 8 hours, preferably 0.5 to 4 hours. Reaction in solution in this manner generally gives good uniformity of degree of substitution as between filaments, and compressed air may be bubbled through the reagent solution to enhance this uniformity. This type of reaction is generally carried out as a batch process.

Alternatively, the reagent solution can be applied by padding, for example to a liquid takeup of 50–300% by weight, optionally followed by mangling, and drying at elevated temperature, for example 50–200° C., preferably at least 80° C. and up to 150° C. The filaments are preferably dried to a moisture content of 5 to 20% by weight to avoid brittleness. The solution containing both sodium hydroxide and sodium monochloroacetate should preferably not be held for an extended time at an elevated temperature. The sodium hydroxide and sodium monochloroacetate solutions can be mixed just before application to the filaments, or the separate solutions can simultaneously be sprayed onto the filaments, for example by sprays arranged at right angles to each other. If the mixed solution of sodium hydroxide and sodium monochloroacetate has to be stored, it is preferably held at a temperature of 20° C. or below, for example 0 to 5° C. Storage at 20–40° C. of filaments treated with both the alkali and the monochloroacetate is preferably avoided. It is usually most convenient to heat the filaments immediately after padding to effect the carboxymethylation reaction. Alternatively, the padded filaments can be stored at a temperature below 20° C., preferably in the range 0 to 5° C., before heating. It may be preferred to carry out padding at a temperature below 20° C., for example 0 to 10° C.

The degree of substitution of the cellulose filaments achieved is preferably at least 0.15 carboxymethyl group per glucose unit, and is most preferably at least 0.2 and less than 0.5. A degree of substitution in the range 0.25 to 0.45 may be particularly suitable. Higher degrees of substitution than 0.5 carboxymethyl group per glucose unit can be used, for example up to 1.0, but they may lead to filaments which are too readily water-soluble rather than water-swellable.

It is believed that the degree of carboxymethylation is not uniform across the cross-section of the filaments; the filaments generally have a higher degree of substitution in the surface region than at the core of the filament. This may be advantageous since the less substituted core contributes greatly to the strength of the filaments in the swollen state. This strength allows the dressing to be pulled from the wound as a coherent dressing. This is an advantage of cellulose filaments which have been carboxymethylated, as against a swellable polymer which has been formed into filaments.

After the carboxymethylation process, the filaments are usually washed to remove any unreacted alkali or chloroacetate or any by-products such as sodium chloride or sodium glycollate. An aqueous wash is generally used, preferably a mixture of water with a water-miscible organic solvent. The washing medium may contain a surfactant and/or an acid. A low molecular weight mono-alcohol such as ethanol or methanol is preferably used as water-miscible organic solvent, for example a preferred washing medium is based on a mixture of water and ethanol in weight ratio 2:1 to 1:2. If a surfactant is used it is preferably a non-ionic surfactant such as a polyalkylene oxide adduct of an alcohol or phenol, although anionic or cationic surfactants can be used. Any surfactant used should preferably be hydrophilic rather than hydrophobic. Examples of preferred surfactants are those sold under the Trade Marks "Tween 20" and "Atlas G1086". Any acid used during washing to neutralise the alkalinity of the carboxymethylated filaments is preferably a weak acid, for example an organic carboxylic acid such as acetic acid or citric acid. The carboxymethylated filaments are preferably neutral for use in most wound dressings; the filament pH is preferably in the range 5.5 to 8. At this pH the carboxymethyl groups are mainly in the anion form rather than free acid form. Dressings of acidic or alkaline pH, as well as neutral dressings, have been suggested for particular wounds, and the amount of acid used in the washing medium can be adjusted to give the desired pH for the filaments.

As an alternative to inclusion of a surfactant in the wash liquid, it may be preferred to apply a surfactant subsequently as a finish. It can for example be applied as a solution in alcohol or in an aqueous alcohol mixture, for example the mixture used to wash the filaments, or a liquid surfactant can be applied undiluted. The finish can be applied by immersion of the filaments in the finish, or it can be applied by lick roller or by spray. If the surfactant is applied as a finish, the filaments are preferably pressed to remove any excess wash liquor, for example by mangling, before applying the finish.

After the required washes, the filaments are generally dried, preferably to a moisture content of 5–20% by weight.

The form of the carboxymethylated filaments after swelling in an aqueous liquid such as saline solution depends on the absorbency of the filaments and the diameter of the filaments. Absorbency generally increases with increasing carboxymethyl group content. At high levels of absorbency, particularly if the filaments are of a low decitex, the swollen filaments tend to form a coherent gel in which the identity of individual filaments cannot be discerned, although the gel retains sufficient fibrous character to be removed as a coherent dressing. For example, filaments of initial decitex 1.7 per filament and having an absorbency (free-swell) of 28, corresponding to treatment with 19.2% by weight $ClCH_2COONa$ and 6.5% NaOH, swell to such a gel. Filaments of the same initial decitex, treated with 13.3% $ClCH_2COONa$ and 4.5% NaOH and having an absorbency of 20, remain as discrete swollen gel filaments. Filaments of initial decitex 6.0, treated with 22.1% $ClCH_2COONa$ and 7.5% NaOH and having an absorbency of 27, also remain as discrete swollen gel filaments. Dressings according to the invention using carboxymethyl cellulose filaments are effective whether they swell to a coherent gel or to discrete gel filaments.

The carboxymethyl cellulose filaments can be used in the dressings in the form of a tow, strand or fabric, for example a yarn of continuous filaments or a yarn formed from staple fibres, or a strand which is a sliver or roving or rope of corded staple fibre, provided that the strand is sufficiently coherent when dry and when swollen to be applied to and removed from a wound, or as a woven, knitted or nonwoven fabric. For example, a cut length of carboxymethyl cellulose filament tow, usually of length at least 3 cm and preferably greater than 10 cm, for example in the range 15 to 30 cm, can be applied directly to the surface of a wound and spread out to cover the whole of the wound. If the wound-contacting surface is formed from a tow of carboxymethyl cellulose filaments, the filaments preferably extend right across the dressing. A rope of carboxymethyl cellulose filaments formed by carding carboxymethyl cellulose staple fibre of length at least 15 mm may be used in a similar way. A dressing of this type would be covered in use with a secondary dressing which is preferably transparent, such as a transparent, water-vapour-permeable film, for example an adhesive-coated polyurethane film such as that sold under the Trade Mark "OpSite".

The carboxymethyl cellulose filaments may be processed into the form of a woven, knitted or nonwoven fabric to produce a flat dressing which may be applied directly to the surface of a wound. A nonwoven fabric can for example be formed by randomly laying, for example dry-laying, or crosslaying the filaments followed by needling. An alternative nonwoven fabric can be formed by crosslaying the carboxymethyl cellulose filaments while partially wet with water, followed by drying, optionally under pressure.

The tow, strand or fabric which forms the wound-contacting surface layer of the dressing of the invention most preferably consists essentially of the carboxymethyl cellulose filaments without any other type of filaments and without any other added material such as adhesive. In such a layer consisting essentially of 100% carboxymethyl cellulose filaments the filaments are generally at least 15 mm long. Alternatively, a woven, knitted or nonwoven fabric dressing may contain up to 80%, preferably up to 50%, by weight, based on total weight, of physiologically inert fibres such as non-carboxymethyl cellulose fibres, polyester fibres, nylon fibres or polyolefin fibres. In such a fabric, the carboxymethyl cellulose filaments are preferably at least 15 mm long, but shorter filaments, for example 10 mm staple fibre, can be used, particularly in a nonwoven fabric. A nonwoven fabric can, for example, be formed by dry-air-laying a mixture of carboxymethyl cellulose fibres and thermoplastic fibres on a permeable conveyor above suction apparatus and consolidating the layer so formed by heating to fuse the thermoplastic fibres at their point of contact. The thermoplastic fibres are preferably polyolefin fibres, for example polyethylene or polypropylene fibres or the bicomponent polyolefin fibres sold under the Trade Mark "Celbond". The dry-laid fabric can alternatively be bonded by consolidating with a latex adhesive.

A fabric of carboxymethyl cellulose filaments for use as a dressing can alternatively be produced by treating a fabric of cellulose filaments with a strong alkali and with monochloroacetic acid or a salt thereof. The fabric treated can for example be a woven, knitted, needled or hydroentangled fabric and can consist wholly of cellulose filaments or may include another fibre, such as polyester, nylon or polyolefin, which is physiologically inert and unaffected by the carboxymethylating reagents. Such other fibre can for example be present at up to 80%, preferably up to 50%, by weight of the fabric.

The carboxymethyl cellulose filaments may be used as one component of a composite dressing in which the carboxymethyl cellulose filament component, for example tow, staple fibre or a rope or fabric, is secured to a backing material such as fabric or a flexible plastics material. The carboxymethyl cellulose filament wound-contacting material, for example in tow or fabric form, can extend across a backing in the form of a frame, for example a polymer foam frame of the type described in EP-A-236104. This may be advantageous for observation of the wound without removal of the dressing if the layer of carboxymethyl cellulose filaments is uncovered or has a transparent film backing extending across the frame.

The wound dressing of the invention can be packaged and sterilised by known techniques, for example by gamma-irradiation. The wound-contacting layer of the dressing can be moistened by sterilised water before application to the wound if desired.

Upon application to the moist surface of a wound the carboxymethyl cellulose filaments absorb the fluid which is exuding from the wound and form a transparent gel. This gel maintains the surface of the wound in a condition which will encourage the natural healing process of the body, that is the surface of the wound is kept in a moist condition without the presence of excess liquid. When the dressing is saturated, or when there is some other reason for its removal, it can be removed from the surface of the wound in one piece due to its inherent strength. Such removal will not damage the newly forming tissue at the surface of the wound because the gel at the surface of the filaments releases readily from the tissue.

Industrial Applicability

Dressings according to the invention are suitable for the treatment of traumatic, surgical and chronic wounds. The preferred application is for wounds which are exuding moderate to high levels of exudate form their surface. Examples of such wounds are venous ulcers, decubitus ulcers, diabetic ulcers, donor graft sites and infected post-operative wounds.

The carboxymethyl cellulose filaments have a further advantage in giving slow release of additives which may be required in a dressing, for example an antiseptic agent or a deodorant, particularly if the additive is applied to the filaments while they are in a swollen state. The additive can for example be included in the last wash liquor applied to the carboxymethyl cellulose filaments, or it can be included in a finish bath if a finish is subsequently applied to the filaments before drying.

EXAMPLES

The invention is illustrated by the following Examples, in which percentages and ratios are by weight.

Example 1

A 33% aqueous solution of sodium hydroxide, a 42% aqueous solution of sodium monochloroacetate and a 95/5 mixture of alcohol (industrial methylated spirits, IMS) and water were mixed to produce an aqueous alcoholic solution containing 6.0% sodium hydroxide and 17.8% sodium monochloroacetate. The solution was added without delay to a reaction vessel containing a dried tow of 1.7 decitex solvent-spun cellulose filaments (spun from tertiary amine oxide solution) and heated to 50° C. The tow was allowed to react at this temperature for 180 minutes.

The tow of carboxymethyl cellulose filaments produced was washed in a solution containing 56% IMS, 43% water, 0.7% acetic acid and 0.3% citric acid. The tow was dried to a moisture content of 15%. The filaments had a free-swell absorbency in 0.9% saline solution of 40 g/g.

The tow was cut to 50 mm lengths and a wound dressing was formed by first carding the cut fibre to form an approximately 18 g.m$^{-2}$ web, then cross folding this web and needling to give a resultant nonwoven fabric of approximately 100 g.m$^{-2}$, and then a 10 cm×10 cm square was cut from the fabric. The square of fabric was packaged in a conventional heat-sealed pouch and sterilised using a gamma radiation dose of 25 kGy.

Alternatively, the tow itself, cut for example to 25 cm lengths, can be used, after packaging and sterilisation, as the wound-contacting surface of a dressing.

Example 2

A tow of solvent-spun filaments having a dry filament decitex of 1.7 was obtained in a never-dried state. The tow was passed through a hand mangle. The amount of water left on the tow after mangling was 62%. This wet tow was put in a solution containing 7.5% sodium hydroxide and 22.1% sodium monochloroacetate at room temperature (20° C.) for 2 minutes. The padded tow was mangled again. The total pick-up after mangling was 75%. The padded and mangled tow was then reacted in a conditioning cabinet set at 23% RH (relative humidity) and 90° C. for five minutes. The amount of water retained on the tow after the treatment was 13%.

After heat treatment the tow was washed in a solution containing 55% industrial alcohol, 42% water, 2.5% acetic acid and 0.5% citric acid. Washed tow was then treated with a finish containing 99% industrial alcohol and 1% Atlas G1086 emulsifier. After this, the tow was dried at a low temperature, leaving some residual moisture on the filaments. The filaments had a tenacity of 17.5 cN/tex and an extensibility of 12%. The degree of substitution was 0.405 carboxymethyl group per glucose unit. The moisture regain of fully dried filaments at 65% RH was 17%. The free-swell absorbency of the filaments in 0.9% saline solution was 38 g/g.

A dressing was formed from the resulting tow as described in Example 1.

Example 3

Following the procedure of Example 2, a tow of never-dried 1.7 decitex solvent-spun filaments was reacted with a solution containing 6.5% sodium hydroxide and 19.2% sodium monochloroacetate. The carboxymethyl cellulose filaments produced had a free-swell absorbency in 0.9% aqueous saline solution of 28 g/g and a degree of substitution of 0.375.

A dressing was formed from the resulting tow as described in Example 1.

Another dressing was formed by cutting the tow to 50 mm staple fibre and carding the resultant fibre to form a sliver or rope. 25 cm lengths of the sliver were packaged and sterilised as described in Example 1.

Example 4

The process of Example 2 was repeated using a tow of never-dried solvent-spun filaments of dry decitex 3.0. The carboxymethyl cellulose filaments produced had a free-swell absorbency in 0.9% aqueous saline solution of 31 g/g.

Dressings in fabric or cut tow form were produced from the treated tow, as described in Example 1.

Example 5

A solution of 6.5% sodium hydroxide and 19.2% sodium monochloroacetate was prepared and cooled to −2° C. in a treatment bath. A tow of never-dried 1.7 decitex solvent-spun filaments was passed at 5 m/min successively through a roller nip of 100 KPa (to reduce the water content to 62% based on dry tow), the above treatment bath, a roller nip of 34 KPa (to give a total solution pick-up of 75%) and a drying cabinet at 90° C./10% RH for 7 minutes. The treated tow was washed as described in Example 2 and was re-dried. The carboxymethyl cellulose filaments produced had a free-swell absorbency in 0.9% saline solution of 34.1 g/g.

A dressing was formed from the tow as described in Example 1.

Example 6

A hydroentangled fabric of dry weight 50 g.m$^{-2}$ formed from 1.7 decitex solvent-spun cellulosic filaments was collected in the wet state. The fabric was immersed in a reagent solution as described in Example 1, heated to 50° C. and allowed to react at this temperature for 180 minutes. The fabric of carboxymethyl cellulose filaments produced was washed in a solution containing 55% IMS, 42% water and 3% acetic acid and dried to a moisture content of 15%. A dressing was formed by cutting a 10 cm×10 cm square from the fabric for packaging and sterilisation as described in Example 1.

Example 7

A dry hydroentangled fabric of solvent-spun cellulose filaments was wetted with water and then immersed in the reagent solution described in Example 1 and further processed to form a dressing as described in Example 6.

Example 8

A square of 5 cm×5 cm was cut from the fabric formed in Example 1 and placed centrally on a 10 cm×10 cm square of "OpSite" adhesive-coated, water-vapour-permeable, polyurethane film. The whole of the exposed surface of the adhesive and the surface of the fabric square was covered with a silicone-coated paper release material. The dressing was packaged and sterilised as in Example 1.

Example 9

The tow of carboxymethyl cellulose filaments produced in Example 1 was cut to 50 mm lengths and 50% of the cut fibre was blended with 50% 1.7 dtex 38 mm "Fibro" (Trade Mark) viscose rayon fibre. The blended fibres were carded, formed into a nonwoven fabric and packaged and sterilised as described in Example 1.

Example 10

The tow of carboxymethyl cellulose filaments produced in Example 1 was cut to 10 mm staple fibre. A blend of 80% of this staple fibre and 20% "Celbond" bicomponent polyolefin fibre was dry-laid at 40 g.m$^{-2}$ by depositing an air suspension of the fibres on a permeable conveyor passing over a suction apparatus. The layer was converted into a nonwoven fabric by passing air at 130° C. through the fabric while it was supported on the permeable conveyor, thereby fusing the "Celbond" fibres to bond the nonwoven fabric.

The nonwoven fabric was cut into squares, packaged and sterilised as described in Example 1.

We claim:

1. A wound dressing having a wound-contacting surface composed of a material selected from the group consisting of a tow of continuous textile filaments at least 15 mm long, a strand formed of textile filaments at least 15 mm long, and a fabric formed of textile filaments at least 3 mm long, substantially all of said textile filaments being carboxymethyl cellulose textile filaments capable of absorbing at least 15 times their own weight of 0.9% by weight aqueous saline solution, as measured by the free-swell absorbency test, to form a swollen transparent gel, wherein the dressing when thus swollen to form a transparent gel retains sufficient fibrous character to be removed as a coherent dressing from a wound.

2. A wound dressing according to claim 1, in which the wound-contacting surface of the dressing is composed of a strand or fabric of carboxymethylated cellulose textile filaments which are at least 15 mm long.

3. A wound dressing according to claim 1, in which the carboxymethylated cellulose textile filaments are at least 30 mm long.

4. A wound dressing according to claim 1, in which the carboxymethylated cellulose textile filaments have a degree of substitution of 0.25 to 0.45 carboxymethyl group per glucose unit.

5. A wound dressing according to claim 1, in which the carboxymethylated cellulose textile filaments have been prepared by reacting cellulose textile filaments with a strong alkali and with monochloroacetic acid or a salt thereof.

6. A wound dressing according to claim 5, in which the cellulose textile filaments are solvent-spun cellulose filaments.

7. A wound dressing having a wound-contacting surface in which said wound-contacting surface comprises one of the group consisting of a tow of textile filaments at least 15 mm long, a strand formed of textile filaments at least 15 mm long and a fabric formed of textile filaments at least 3 mm long, said textile filaments comprising carboxymethylated cellulose textile filaments which have been prepared by reacting polynosic viscose rayon textile filaments with a strong alkali and with monochloroacetic acid or a salt thereof and which are capable of absorbing at least 15 times their own weight of 0.9% by weight aqueous saline solution, as measured by the free-swell absorbency test, to form a swollen transparent gel, wherein the dressing when thus swollen to form a transparent gel retains sufficient fibrous character to be removed as a coherent dressing from a wound.

8. A wound dressing according to claim 1, in which the carboxymethylated cellulose textile filaments are in the form of a tow, strand or fabric which is capable of absorbing at least 25 times its own weight of 0.9% by weight aqueous saline solution, as measured by the free-swell absorbency test.

9. A wound dressing according to claim 1, comprising a backing material and a tow of carboxymethylated cellulose textile filaments which extend across the wound-contacting surface of the dressing.

10. A wound dressing having a wound-contacting surface composed of a material from the group consisting of a tow of textile filaments at least 15 mm long, a strand formed of textile filaments at least 15 mm long and a fabric formed of textile filaments at least 3 mm long, substantially all of said textile filaments consisting of at least 50% by weight carboxymethylated cellulose textile filaments and up to 50% by weight physiologically inert fibres selected from the group consisting of non-carboxymethylated cellulose fibres, polyester fibres, nylon fibres and polyolefin fibres, said carboxymethylated cellulose textile filaments being capable of absorbing at least 15 times their own weight of 0.9% by weight aqueous saline solution, as measured by the free-swell absorbency test, to form a swollen transparent gel, wherein the dressing when thus swollen to form a transparent gel retains sufficient fibrous character to be removed as a coherent dressing form a wound.

11. A wound dressing according to claim 1, in which the wound-contacting surface of the dressing is a fabric composed of textile filaments, substantially all of which are carboxymethylated cellulose textile filaments.

12. A wound dressing according to claim 11, in which the fabric is a nonwoven fabric.

13. A wound dressing according to claim 11, in which the fabric has been prepared by reacting a fabric of cellulose textile filaments with a strong alkali and with monochloroacetic acid or a salt thereof.

14. A wound dressing according to claim 11, in which the fabric has been prepared by converting carboxymethylated cellulose textile filaments to fabric in a weaving, knitting or nonwoven fabric process.

15. A process for the treatment of a traumatic, surgical or chronic wound which is exuding from its surface, comprising applying to the wound a wound dressing having a wound-contacting surface composed of a fabric formed of textile filaments at least 3 mm long, substantially all of the textile filaments forming the fabric being carboxymethylated cellulose textile filaments capable of absorbing at least 15 times their own weight of 0.9% by weight aqueous saline solution (as measured by the free-swell absorbency test) to form a swollen transparent gel, wherein the dressing when thus swollen to form a transparent gel retains sufficient fibrous character to be removed as a coherent dressing from a wound.

16. A process for the treatment of a traumatic, surgical or chronic wound which is exuding from its surface, comprising applying to the wound a wound dressing having a wound-contacting surface composed of carboxymethylated cellulose textile filaments at least 15 mm long, the filaments being capable of absorbing at least 15 times their own weight of 0.9% by weight aqueous saline solution, as measured by the free-swell absorbency test, to form a transparent gel which retains sufficient fibrous character to be removed as a coherent dressing from the wound.

17. A process according to claim 16, comprising applying to the surface of the wound said carboxymethylated cellulose textile filaments in the form of a tow of filaments or a rope of filaments in staple fibre form and spreading said filaments to cover the wound.

18. A process according to claim 16, wherein said wound is a cavity wound having an inner surface, the process comprising applying a tow of carboxymethylated cellulose textile filaments or a rope of carboxymethylated cellulose textile filaments in staple fibre form to fill or line the inner surface of the cavity wound.

19. A wound dressing according to claim 10, in which the carboxymethyl cellulose filaments have a degree of substitution of 0.25 to 0.45 carboxymethyl group per glucose unit.

20. A wound dressing according to claim 10, in which the carboxymethyl cellulose filaments have been prepared by reacting cellulose filaments with a strong alkali and with monochloroacetic acid or a salt thereof.

21. A wound dressing according to claim 20, in which the cellulose filaments are solvent-spun cellulose filaments.

22. A wound dressing according to claim 10 in which the wound-contacting surface of the dressing is a fabric composed of the said carboxymethylated cellulose textile filaments and the said physiologically inert fibres.

23. A wound dressing according to claim 22 in which the fabric is a nonwoven fabric.

24. A wound dressing having a wound-contacting surface comprising one of the group consisting of a tow of textile filaments at least 15 mm long, a strand formed of textile filaments at least 15 mm long and a fabric formed of textile filaments at least 3 mm long, said textile filaments comprising at least 50% by weight carboxymethylated cellulose textile filaments and up to 50% by weight physiologically inert fibres selected from non-carboxymethylated cellulose fibres, polyester fibres, nylon fibres and polyolefin fibres, said carboxymethylated cellulose textile filaments being capable of absorbing at least 15 times their own weight of 0.9% by weight aqueous saline solution, as measured by the free-swell absorbency test, to form a swollen transparent gel, wherein the dressing when thus swollen to form a transparent gel retains sufficient fibrous character to be removed as a coherent dressing from a wound; in which the wound-contacting surface of the dressing is a fabric comprising the said carboxymethylated cellulose textile filaments and the said physiologically inert fibres; and in which the fabric has been prepared by reacting a fabric of cellulose textile filaments and physiologically inert fibres selected from polyester fibres, nylon fibres and polyolefin fibres with a strong alkali and with monochloroacetic acid or a salt thereof.

25. A wound dressing according to claim 22 in which the fabric has been prepared by converting carboxymethylated cellulose textile filaments and the said physiologically inert fibres to fabric in a weaving, knitting or nonwoven fabric process.

26. A process for the treatment of a traumatic, surgical or chronic wound which is exuding from its surface, comprising applying to the wound a wound dressing having a wound-contacting surface composed of a fabric formed of textile filaments at least 3 mm long, substantially all of the textile filaments forming the fabric being carboxymethylated cellulose textile filaments or physiologically inert fibres selected from non-carboxymethylated cellulose fibres, polyester fibres, nylon fibres and polyolefin fibres, at least 50% by weight of the textile filaments forming the fabric being carboxymethylated cellulose textile filaments said carboxymethylated cellulose textile filaments being capable of absorbing at least 15 times their own weight of 0.9% by weight aqueous saline solution, as measured by the free-swell absorbency test, to form a swollen transparent gel, wherein the dressing when thus swollen to form a transparent gel retains sufficient fibrous character to be removed as a coherent dressing from the wound.

27. A wound dressing according to claim 1, in which substantially all of said textile filaments are non-crosslinked carboxymethyl cellulose textile filaments.

28. A wound dressing according to claim 7, in which substantially all of said textile filaments are non-crosslinked carboxymethyl cellulose textile filaments.

29. A wound dressing according to claim 10, in which substantially all of said carboxymethylated cellulose textile filaments are non-crosslinked.

30. A wound dressing according to claim 24, in which substantially all of said carboxymethylated cellulose textile filaments are non-crosslinked.

31. The process according to claim 15, in which substantially all of said textile filaments are non-crosslinked carboxymethyl cellulose textile filaments.

32. The process according to claim 16, in which substantially all of said carboxymethylated cellulose textile filaments are non-crosslinked carboxymethyl cellulose textile filaments.

33. The process according to claim 24, in which substantially all of said carboxymethylated cellulose textile filaments forming the fabric are non-crosslinked carboxymethyl cellulose textile filaments.

\* \* \* \* \*

UNITED STATES PATENT AND TRADEMARK OFFICE
CERTIFICATE OF CORRECTION

PATENT NO. : 6,075,177
DATED : June 13, 2000
INVENTOR(S) : H. Bahia et al.

It is certified that error appears in the above-indentified patent and that said Letters Patent is hereby corrected as shown below:

On the title page, item [30],
      after the section headed "Related U.S. Application Data" insert
--(30) Foreign Application Priority Data
  Jan. 22, 1993         United Kingdom........................9301258.1--

Column 14, line 1, change "24" to --26--

Signed and Sealed this

Twentieth Day of February, 2001

Attest:

NICHOLAS P. GODICI

Attesting Officer    Acting Director of the United States Patent and Trademark Office